(12) United States Patent
McDougald et al.

(10) Patent No.: US 8,735,600 B2
(45) Date of Patent: May 27, 2014

(54) PROCESS FOR PURIFICATION OF 1-METHYLPYRAZOLE-4-CARBOXYLIC ACID ESTERS

(75) Inventors: Graham McDougald, Bracknell (GB); James Peter Muxworthy, Bracknell (GB); Beverley Ann Wilde, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 73 days.

(21) Appl. No.: 13/320,730

(22) PCT Filed: Apr. 20, 2010

(86) PCT No.: PCT/EP2010/055174
§ 371 (c)(1),
(2), (4) Date: Nov. 15, 2011

(87) PCT Pub. No.: WO2010/130532
PCT Pub. Date: Nov. 18, 2010

(65) Prior Publication Data
US 2012/0065407 A1    Mar. 15, 2012

(30) Foreign Application Priority Data

May 15, 2009   (GB) .................................. 0908435.1

(51) Int. Cl.
C07D 231/14    (2006.01)
C07D 409/12    (2006.01)

(52) U.S. Cl.
USPC .................................... 548/365.7; 548/374.1

(58) Field of Classification Search
None
See application file for complete search history.

(56) References Cited

U.S. PATENT DOCUMENTS 8,124,787 B2 *   2/2012   Giordano et al. .......... 548/374.1

FOREIGN PATENT DOCUMENTS

| EP | 1072576    | 1/2001    |
| EP | 1854788    | 11/2007   |
| JP | 2004099567 | * 4/2004  |
| WO | 2008022777 | 2/2008    |
| WO | 2008053043 | 5/2008    |
| WO | 200900442  | 12/2008   |

OTHER PUBLICATIONS

Purification of Laboratory Chemicals by W.L.F. Armarego, Christina Chai, Fifth edition, 2003.*

* cited by examiner

*Primary Examiner* — Kamal Saeed
(74) *Attorney, Agent, or Firm* — R. Kody Jones

(57) ABSTRACT

The present invention relates to improvements in processes towards the production 3-difluoromethyl-1-methyl-1H-pyrazole-4-carboxylic acid, which is a useful intermediate in fungicide production. In particular, the invention relates to a process for treating a compound of formula III, wherein $R^1$ is $C_1$-$C_6$ alkyl and $R^2$ is $CF_3$, $CF_2H$ or $CFH_2$, comprising the steps of a) contacting a compound of formula III with base, and b) separating the compound of formula III and the base.

(III)

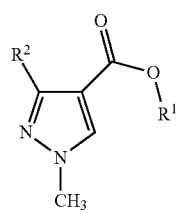

13 Claims, 1 Drawing Sheet

PROCESS FOR PURIFICATION OF 1-METHYLPYRAZOLE-4-CARBOXYLIC ACID ESTERS

Figure 1A:
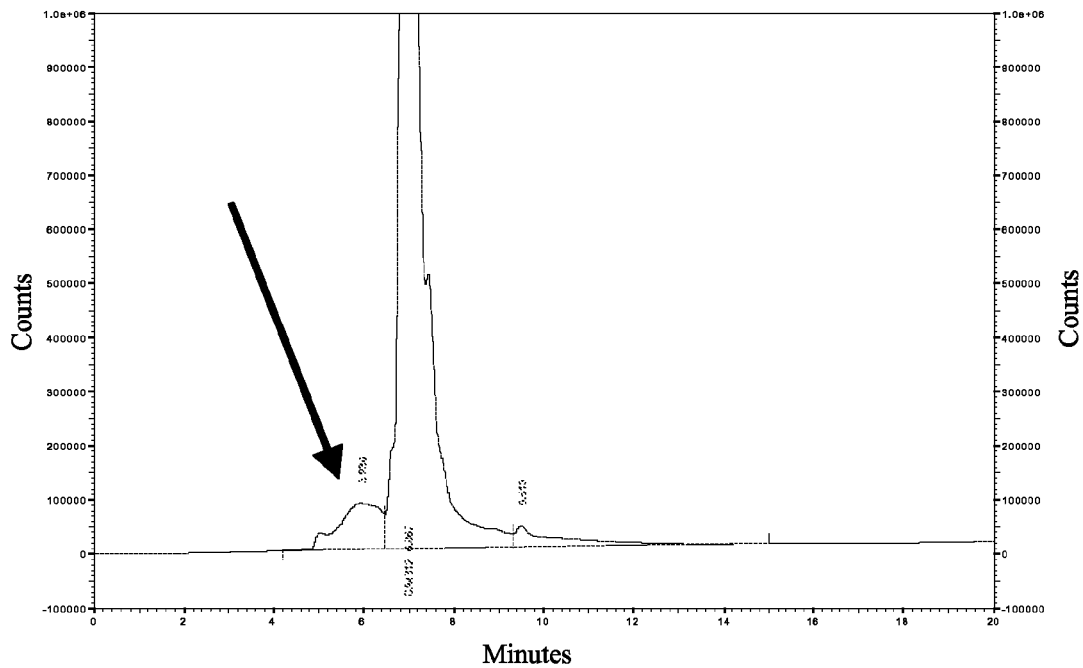

This application is a 371 of International Application No. PCT/EP2010/055174 filed Apr. 20, 2010, which claims priority to GB 0908435.1, filed May 15, 2009, the contents of which are incorporated herein by reference.

The present invention relates to improvements in processes towards the production of compounds including 3-difluoromethyl-1-methyl-1H-pyrazole-4-carboxylic acid, which is useful as an intermediate in fungicide production. More specifically the invention relates to a method of treating compounds including 3-difluoromethyl-1-methyl-1H-pyrazole-4-carboxylic acid ethyl ester.

Said 3-difluoromethyl-1-methyl-1H-pyrazole-4-carboxylic acid (DFPA—compound of formula I) can be used for the production of fungicides, which are described, for example, in WO 03/74491, WO 04/35589, WO 03/70705, WO 07/17450, WO 06/120219 and WO 06/87343.

Fungicides are generally produced in large quantities. For example, the fungicide chlorothalonil has been produced in the year 2005 in a quantity of over 23,000 metric tons. Given the scale on which fungicides are produced, any improvement to the production process can represent significant cost savings.

DFPA is a key intermediate in the production of many fungicides. Methods for the synthesis of DFPA are known, e.g. from the documents cited above, and others such as WO 2008/145257. However, known processes for the production of DFPA do not always result in a product of optimal purity for carrying forward to subsequent processes in the production of fungicidal active ingredients. In particular we have found that impurities present in DFPA can cause problems with tarring when making the corresponding acid chloride and in further downstream processes towards the production of fungicides. Processes for the production of the acid chloride are described, for example, in WO 04/35589.

We have now surprisingly found that treating the ester precursor of DFPA with base substantially reduces tarring when making the corresponding acid chloride from DFPA.

Accordingly, the present invention provides a process for treating a compound of formula III

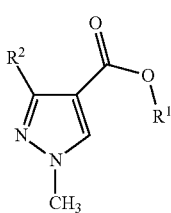

(III)

wherein $R^1$ is $C_1$-$C_6$ alkyl and $R^2$ is $CF_3$, $CF_2H$ or $CFH_2$, comprising the steps of contacting a compound of formula III with base and subsequently separating the compound of formula III and the base.

Processes for obtaining the compound of formula III and for converting the compound of formula III to DFPA and analogues thereof are described, for example, in WO 2008/145257.

The compound of formula III readily dissolves in organic solvents that are immiscible with water, and is itself immiscible with water. Thus, using a base that is water soluble, e.g. an aqueous alkali, allows the compound of formula III and base to be conveniently separated by phase separation.

Accordingly, in a further embodiment the invention provides a method for treating, e.g. washing, a compound of formula III:

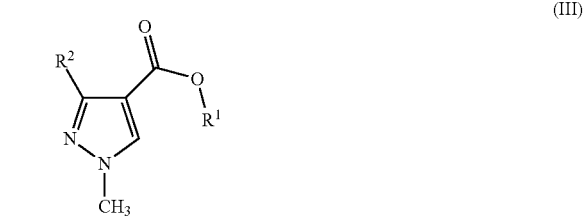

(III)

wherein $R^1$ is $C_1$-$C_6$ alkyl and $R^2$ is $CF_3$, $CF_2H$ or $CFH_2$, comprising the steps of:
a) contacting the compound of formula III with an aqueous base;
b) separating the compound of formula III and the base.

The compound of formula III and the base may be separated by removing the aqueous phase. This may be achieved e.g. by gravity separation of the aqueous phase and organic phases followed by removal of the aqueous phase. Such techniques are well known to the person skilled in the art.

The base may be added to the compound of formula III as an aqueous solution, or base and water may be added to the compound of formula III separately, e.g. water may be added followed by the base. Preferably, the base is added to the compound of formula III as an aqueous solution. The amount of water used is preferably enough to allow good mixing efficiency. A person skilled in the art would readily be able to choose a suitable amount of water for this purpose.

The amount of base is preferably chosen such that a large amount of impurities are removed without causing significant hydrolysis of the compound of formula III. For example, the amount of base used may be less than 1, 0.9, 0.8, 0.7, 0.6, 0.5, 0.4, 0.3, or even less than 0.2 molar equivalents of base relative to the amount of the compound of formula III. The amount base used may be more than 0.001, 0.01, 0.05, 0.09 or more than 0.1 molar equivalents of base relative to the amount of the compound of formula III. For example, the amount of base used may be 0.05 to 1 molar equivalents of base relative to the amount of the compound of formula III, e.g. 0.05 to 0.9, 0.05 to 0.8, 0.05 to 0.7, 0.05 to 0.6, 0.05 to 0.5, 0.05 to 0.4, 0.05 to 0.3, 0.05 to 0.2 molar equivalents of base relative to the compound of formula III, e.g. 0.1 to 0.8, 0.1 to 0.7, 0.1 to 0.6, 0.1 to 0.5, 0.1 to 0.4, 0.1 to 0.3, or 0.1 to 0.2 molar equivalents of base relative to the compound of formula III. Preferably the amount of base used is 0.1 to 0.5 molar equivalents, e.g. 0.1 to 0.3 molar equivalents of base relative to the compound of formula III.

For example, when an aqueous based is used, the base strength in the aqueous phase prior to addition to the compound of formula III may be less than 50%, 40%, 30%, 20%, 15%, 10%, 8%, 5%, 4%, 3%, or less than 2%. The base strength used may be more than 0.01%, 0.1%, 0.3%, 0.8%, or even more than 1%. Preferably the base strength is less than 15%. For example, the base strength may be in the range 0.01% to 50%, 0.01 to 30%, 0.1 to 25%, 0.1 to 15%, 0.5 to 15%. The base strength refers to the mass of base divided by total mass of base and water.

For example, when an aqueous base is used the concentration of base in the aqueous phase prior to addition to the compound of formula III may be less than 12.5 M, 10M, 7.5M, 5M, 2.5M, 2M, 1.5M, 1M, 0.5M, or less 0.25M, or less than 0.1M. The amount of base used may be more than 0.001M, 0.01M, 0.05M, 0.06M, 0.07M, 0.08M, 0.09M, e.g. more than 0.1M. The concentration may be in the range 0.01M to 12.5M, 0.01 to 8M, 0.1M to 5M, 0.1 to 3.5M, or 0.5M to 3M.

The base is preferably a water soluble base, e.g. a water immiscible base, such as an alkali. The base is preferably an inorganic base. For example, the base is one which forms hydroxide ions when dissolved in water. Preferably, the base is a salt of an alkali metal or an alkali earth metal, e.g. a salt of any of Li, Na, K, Rb, Cs, Mg, Sr, and Ba, in particular Na or K. The base may be a carbonate or hydroxide salt, preferably a hydroxide salt. Specific examples include NaOH, KOH, $Na_2CO_3$, $K_2CO_3$, in particular NaOH and KOH. Usually just one type of base will be employed, but the method may also be performed using more than one type of base.

The compound of formula III may be provided as a solution comprising solvent and compound of formula III. The solvent is preferably a water-immiscible organic solvent. The term "water-immiscible" means that when the organic solvent is mixed with water under the conditions of the process according to the invention two separate liquid phases are formed.

Suitable organic solvents include optionally halogenated aromatic hydrocarbon solvents, ketone solvents, optionally halogenated hydrocarbon solvents or ether solvents. In said definitions, halogen is generally fluorine, chlorine, bromine and/or iodine, preferably fluorine, bromine and/or chlorine. Examples of "optionally halogenated aromatic hydrocarbon solvents" include benzene, toluene, xylene, chlorobenzene and dichlorobenzene. Toluene and xylene, including mixed xylenes are preferred.

An example of a "ketone solvent" is methylisobutylketone. Examples of "optionally halogenated hydrocarbon solvents" are pentane, hexane, octane, cyclohexane, methylcyclohexane, heptane, chloroform and carbon tetrachloride; more preferred is cyclohexane and methylcyclohexane. A preferred "ether solvent" is dioxane.

The step of contacting the compound of formula III with base may include mixing the compound of formula III with the base. When the process is a batch process mixing may be achieved e.g. using a mechanical stirrer. When the process is a continuous process, mixing may be achieved for example using a static mixer, e.g. the compound of formula III may be fed through a series of static agitators after or whilst base is added to the compound of formula III. As mentioned above, the compound of formula III may be provided as a solution comprising the compound of formula III and water immiscible organic solvent.

The contacting step, e.g. including mixing, may be performed at a temperature in the range −25 to 80° C., e.g. 0 to 60° C., e.g. 10 to 40° C., e.g. 15 to 35° C., e.g. 15 to 30° C., e.g. 20 to 30° C. The contacting step may be conveniently performed at ambient temperature. The duration of the contacting step, e.g. including mixing, may be more than 1 second, e.g. more than 1 minute, e.g. more than 5, 10, 20, 30, 40, 50, 60, 70, 80, 90, 100 minutes, or even more than 110 minutes. For example the duration of the mixing step may be 1 second to 48 hours, 1 to 500 minutes, 1 to 300 minutes, 1 to 200 minutes, 10 to 150 minutes, e.g. 30 to 150 minutes.

The method can be carried out at normal, elevated or reduced pressure, preferably at normal pressure.

In a further aspect of the invention there is provided a method comprising washing a compound of formula III

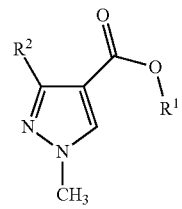
(III)

wherein $R^1$ is $C_1$-$C_6$ alkyl and $R^2$ is $CF_3$, $CF_2H$ or $CFH_2$, with aqueous alkali.

In a further aspect of the invention there is provided a method of washing a compound of formula III:

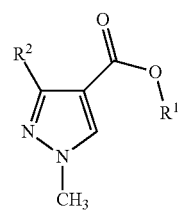
(III)

wherein $R^1$ is $C_1$-$C_6$ alkyl and $R^2$ is $CF_3$, $CF_2H$ or $CFH_2$, comprising the steps of:
a) providing a solution comprising the compound of formula III and a water-immiscible organic solvent,
b) adding an aqueous base to said solution,
bb) mixing the aqueous phase and organic phases,
bbb) removing the aqueous phase,
wherein the base is a hydroxide or carbonate of an alkali metal or alkali earth metal, e.g. NaOH, $Na_2CO_3$, KOH, $K_2CO_3$, and wherein the amount of base in the mixture of step b) is 0.1 to 0.5 molar equivalents relative to the amount of the compound of formula III.

In a further aspect of the invention there is provided a method of purifying a compound of formula III

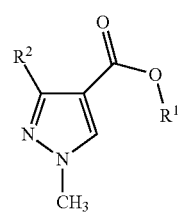
(III)

wherein $R^1$ is $C_1$-$C_6$ alkyl and $R^2$ is $CF_3$, $CF_2H$ or $CFH_2$, for use as a reactant in a process for the production of a compound of formula I

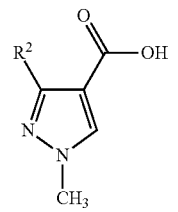
(I)

wherein $R^2$ is $CF_3$, $CF_2H$ or $CFH_2$,
comprising treating a compound of formula III as described above.

The invention may include, prior to treating the compound of formula III, the steps of producing the compound of formula III, comprising reacting a compound of formula II

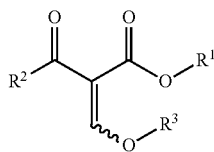
(II)

wherein $R^1$ and $R^3$ are both independently $C_1$-$C_6$alkyl and $R^2$ is $CF_3$, $CF_2H$ or $CFH_2$, with methylhydrazine to form a compound of formula III, e.g. as described in WO 2008/145257, e.g. the compound of formula II may be reacted with methylhydrazine in the presence of water and a water-immiscible organic solvent.

Thus, in a further aspect of the invention, there is provided a process comprising
i. producing a compound of formula III

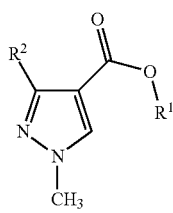
(III)

wherein $R^1$ is $C_1$-$C_6$ alkyl and $R^2$ is $CF_3$, $CF_2H$ or $CFH_2$, comprising reacting a compound of formula II

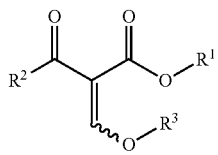
(II)

wherein $R^1$ and $R^3$ are both independently $C_1$-$C_6$alkyl and $R^2$ is $CF_3$, $CF_2H$ or $CFH_2$, with methylhydrazine to form a compound of formula III; and
ii. treating the compound of formula III as described above.

The invention may include, after treating the compound of formula III, producing a compound of formula I

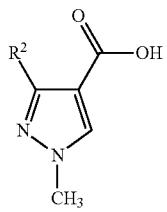
(I)

wherein $R^2$ is $CF_3$, $CF_2H$ or $CFH_2$,
comprising hydrolysing the compound of formula III to provide a compound of formula I, e.g. as described in WO 2008/145257 and WO 04/35589.

Hydrolysis of the compound of formula III may be achieved by performing the steps:

c) saponifying that compound in situ leading to the formation of a compound of formula I by c1) adding a base to form the anion of the compound of formula I;

c2) adding an acid to form the compound of formula I;

e.g. as described in WO 2008/145257.

Accordingly, in a further aspect, the invention provides a method of producing a compound of formula I

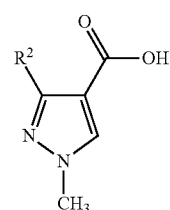
(I)

wherein $R^2$ is $CF_3$, $CF_2H$ or $CFH_2$,
comprising
ii. treating a compound of formula III

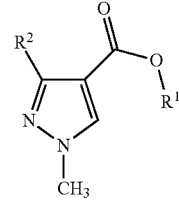
(III)

wherein $R^1$ is $C_1$-$C_6$ alkyl and $R^2$ is $CF_3$, $CF_2H$ or $CFH_2$,
as described above, and
iii. hydrolysing the compound of formula III to produce the compound of formula I.

In a further aspect of the invention, there is provided a method of producing a compound of formula I,

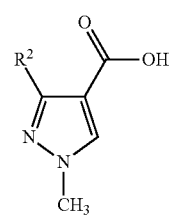
(I)

wherein $R^2$ is $CF_3$, $CF_2H$ or $CFH_2$,
comprising i. producing a compound of formula III

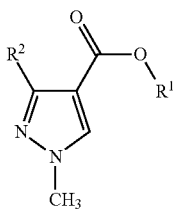
(III)

wherein $R^1$ is $C_1$-$C_6$ alkyl and $R^2$ is $CF_3$, $CF_2H$ or $CFH_2$, comprising reacting a compound of formula II

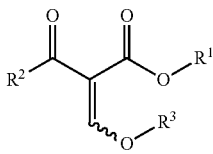
(II)

wherein $R^1$ and $R^3$ are both independently $C_1$-$C_6$ alkyl and $R^2$ is $CF_3$, $CF_2H$ or $CFH_2$, with methylhydrazine to form a compound of formula III,
ii. treating the compound of formula III as described above, and
iii. hydrolysing the compound of formula III to provide the compound of formula I.

In a further aspect, the invention provides a method of producing a compound of formula IV

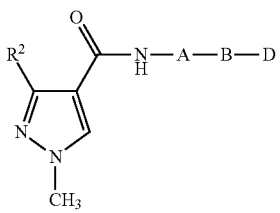
(IV)

wherein $R^2$ is $CF_3$, $CF_2H$ or $CFH_2$,
A is thienyl, phenyl, or ethylene each optionally substituted by one to three groups independently selected from halogen, methyl and methoxy,
B is a direct bond, cyclopropylene, an annelated bicyclo[2.2.1]heptane- or bicyclo[2.2.1]heptene ring,
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio,
comprising producing a compound of formula I

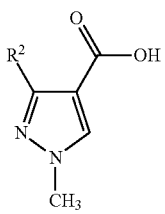
(I)

wherein $R^2$ is $CF_3$, $CF_2H$ or $CFH_2$, according to the invention, and iv) reacting the compound of formula I or corresponding acid-halide with a compound of formula V $$H_2N\text{-}A\text{-}B\text{-}D \qquad (V)$$

wherein A, B and D are as defined for the compound of formula IV.

The compound of formula IV is preferably a compound of formula VI (Isopyrazam), a compound of formula VII (Sedaxane), a compound of formula VIII, a compound of formula IX (Penthiopyrad), a compound of formula X (Bixafen), a compound of formula XI (Fluxapyroxad), a compound of formula XII, or a compound of formula XIII.

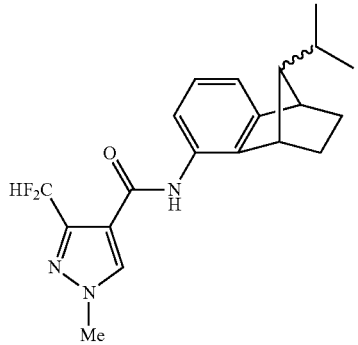
(VI)

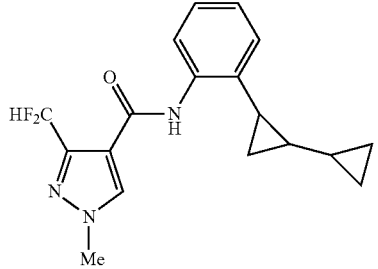
(VII)

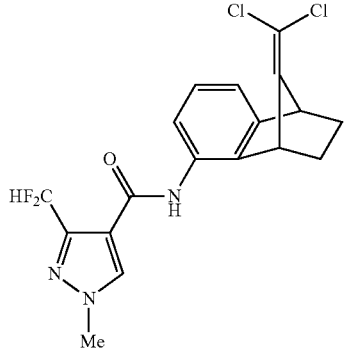
(VIII)

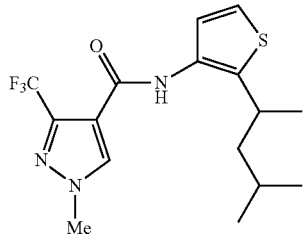
(IX)

-continued

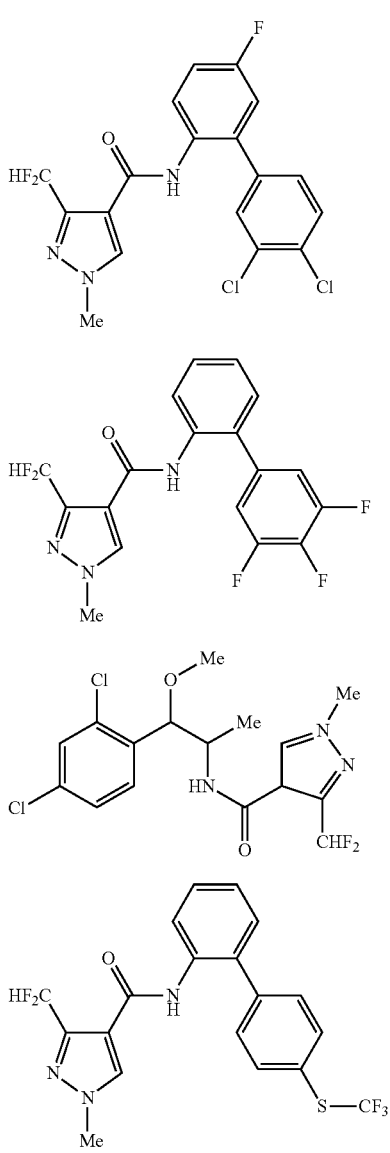

(X)

(XI)

(XII)

(XIII)

Step iv) may be performed according to known methods, e.g. as described in WO 2004/035589 or WO 2009/135860. For example, the compound of formula I may be treated with a halogenating agent, such as thionyl chloride, oxalyl chloride, phosgene, SF$_4$, DAST, deoxofluor or thionylbromide to provide the acid-halogen, e.g. the acid chloride, which may then be reacted with the compound of formula V in the presence of a suitable base, e.g. LiOH, KOH, NaOH, NEt$_3$, NaHCO$_3$, KHCO$_3$, Na$_2$CO$_3$ or K$_2$CO$_3$, e.g. in a solvent such as toluene, xylenes, dichloromethane, ethyl acetate or DMF, e.g. at −10° C. to 30° C.

Isopyrazam, Sedaxane, Penthiopyrad, Fluxapyroxad and Bixafen are known fungicides. The compound of formula VIII is known, e.g. from WO 2007/048556, the compound of formula XII is known e.g. from WO 2010/000612, the compound of formula XIII is known e.g. from WO 2008/053044.

The alkyl groups appearing in the above substituent definitions may be straight-chain or branched and are, for example, methyl, ethyl, n-propyl, isopropyl, n-butyl, sec-butyl, isobutyl or tert-butyl, preferably methyl or ethyl. In preferred processes R$^1$ and/or R$^3$ are ethyl. In preferred processes R$^2$ is CF$_2$H.

Compounds of formula II occur in two isomers with regard to the double bond substituted by the alkoxy group —O—R$^3$: the E- and the Z-isomer. Both isomers or mixtures thereof can be used in the processes according to the invention.

Specific embodiments of process steps i. and iii. are described in more detail below. These embodiments correspond to process steps a) and b) as described in WO 2008/145257.

Process Step i.:

In step i., methylhydrazine can be used in equimolar amounts, in sub-equimolar amounts or in excess relative to compounds of formula II, preferably methylhydrazine is used in equimolar amounts. Thus the molar ratio of methyl hydrazine:compound of formula II is preferably from 1:0.8 to 1:1.2.

In one embodiment, methylhydrazine is used in the form of an aqueous solution, such as a 35% (w/w) or 40% (w/w) aqueous solution.

Preferably the solvent is the same as used during treating the compound of formula III as described above.

The compounds of formula II are known or can be prepared analogously to processes known in the literature. For example, such compounds can be prepared from the 3-oxo-carboxylic acid esters on which they are based as described in WO 93/11117.

Process step i. is preferably carried out in a temperature range of from −20° C. to 50° C., preferably from 0° C. to 50° C., especially from 10° C. to 25° C.

The reaction time for process step i. is generally from 15 minutes to 48 hours, preferably 15 minutes to 18 hours, more preferably 15 minutes to 5 hours or from 1 to 5 hours. Said step can be carried out at normal, elevated or reduced pressure. In one embodiment, said step is carried out at normal pressure.

In one embodiment a base is used in process step i. The base is preferably selected from inorganic bases, such as hydroxides, for example LiOH, NaOH or KOH. Bases to which preference is given are hydroxides, such as NaOH or KOH; especially preferred is NaOH.

When a base is used in step i. preferably at least one equivalent of water is added at the start of the reaction relative to compounds of formula II; more preferably at least 10 equivalents of water are added, more preferably from 10 to 30 equivalents of water are added.

When a base is used in process step i. the molar ratio between water added at the start of the reaction and the organic solvent is preferably from 20:1 to 1:20; more preferably from 10:1 to 1:10. In one embodiment said molar ratio is from 10:1 to 1:1. This molar ratio according to the invention does not include the water being formed by the consumption of compounds of formula II by the condensation reaction of step i. Maximally one equivalent of water relative to compounds of formula II can be formed.

An example of performing step i. using a base comprises:
preparing an aqueous solution comprising methylhydrazine and the base,
preparing a solution of the compound of formula II in the organic solvent, and
mixing both solutions.

In said embodiment, the aqueous solution comprising methylhydrazine and the base can be added to the solution of the compound of formula II in the organic solvent or vice versa. In one embodiment, the solution of the compound of formula II in the organic solvent is added to the aqueous solution comprising methylhydrazine and the base.

Preferably the base is present in step i. in an amount of 0.1 to 0.5 equivalents relative to the compounds of formula II used.

In another preferred embodiment process i. is performed without the addition of a base. In this embodiment it is preferred to have a molar ratio of methylhydrazine:compound of formula II of from 1:0.8 to 1:1.2, preferably 1:1. The molar ratio of methylhydrazine to organic solvent is preferably from 1:1 to 1:20, more preferably 1:1 to 1:5, even more preferably from 1:1 to 1:2. The mass ratio of methylhydrazine 35% to organic solvent is preferably from 1:1 to 1:20, more preferably 1:1 to 1:5, even more preferably from 1:1 to 1:1.5. The molar ratio of compound of formula II to organic solvent is preferably from 1:1 to 1:20, more preferably 1:1 to 1:5, even more preferably from 1:2 to 1:4. The mass ratio of compound of formula II to organic solvent is preferably from 1:1 to 1:20, more preferably 1:1 to 1:5, even more preferably from 1:1 to 1:2.

In this embodiment it is preferred to perform the process at −20° C. to 50° C., preferably from 0° C. to 50° C., more preferably from 0° C. to 25° C. and especially 10-25° C.

When no base is used in step i. it is not essential to add any extra water if an aqueous solution of methylhydrazine such as a 35% (w/w) or 40% (w/w) aqueous solution is used. However if 40% w/w methylhydrazine is used as a starting material it is preferred to add sufficient water to dilute the methyl hydrazine to 35% w/w.

An example of a step i. according to this embodiment is a process step comprising:
preparing a solution comprising methylhydrazine in water and the organic solvent,
preparing a solution of the compound of formula II in the organic solvent, and
mixing both solutions.

In said embodiment, the solution comprising methylhydrazine can be added to the solution of the compound of formula II in the organic solvent or vice versa. In one embodiment, the solution of the compound of formula II in the organic solvent is added to the solution comprising methylhydrazine.

Process Step iii:

Process step iii, hydrolysis of the compound of formula III, may be carried out without isolation of compounds of formula II or III (the compounds of formula II and/or III are used in situ). This leads to significant cost savings taken especially into account the large-scale production of fungicides. Step iii. can be carried out as described under step c), e.g. under c1) (alkaline saponification) or under step c2) (acidic saponification).

Process Step c1):

Step c1) can be divided into two sub-steps: i) the formation of the anion of the compound of formula I ("the anion") by adding a base and ii) the formation of the compound of formula I ("the free acid") by later adding an acid.

The base is preferably selected from inorganic bases, such as hydroxides, for example LiOH, NaOH or KOH. Bases to which preference is given are hydroxides, such as NaOH or KOH; especially preferred is NaOH.

A suitable amount of base for anion formation is, for example, at least one equivalent relative to compounds of formula III, preferably from 1 to 5 equivalents; more preferably from 1 to 3 equivalents.

The formation of the anion is preferably carried out in a temperature range of from 40° C. to 100° C., especially from 40° C. to 70° C. The reaction time for anion formation is generally from 15 minutes to 48 hours, preferably from 15 minutes to 18 hours, more preferably 15 minutes to 5 hours or 1 to 5 hours. Said anion formation can be carried out at normal, elevated or reduced pressure, preferably at normal pressure.

After formation of the anion, said anion is typically present in the aqueous phase of the reaction mixture. In a preferred embodiment of the invention, the aqueous phase is isolated from the organic phase before the acid is added.

In one embodiment of the invention, the acid is added leading to an adjustment of the pH of the aqueous phase to a value of 7 or below, preferably 6 or below, more preferably 5 or below.

Suitable acids are inorganic acids, such as hydrochloric acid or sulfuric acid; or organic acids, such as formic acid, acetic acid or propionic acid. Preference is given to inorganic acids and special preference is given to hydrochloric acid.

The acid is added preferably in a temperature range of from 50° C. to 95° C., especially from 80° C. to 95° C.

The reaction time for formation of the free acid is generally from 15 minutes to 48 hours, preferably from 15 minutes to 18 hours, more preferably 15 minutes to 5 hours or from 1 to 5 hours. Said free acid formation can be carried out at normal, elevated or reduced pressure, preferably at normal pressure.

Base is added for anion formation so that the amount of base is present of at least 1 equivalent relative to the amount of compounds of formula II, preferably from 1 to 5 equivalents; more preferably from 1 to 3 equivalents.

After formation of the anion, said anion is typically present in the aqueous phase of the reaction mixture. In a preferred embodiment of the invention, the aqueous phase is isolated from the organic phase before the acid is added.

The acid may be added leading to an adjustment of the pH of the aqueous phase to a value of 7 or below, preferably 6 or below, more preferably 5 or below.

Suitable acids are inorganic acids, such as hydrochloric acid or sulfuric acid; or organic acids, such as formic acid, acetic acid or propionic acid. Preference is given to inorganic acids and special preference is given to hydrochloric acid.

The acid is added preferably in a temperature range of from 50° C. to 95° C., especially from 80° C. to 95° C.

The reaction time for formation of the free acid is generally from 15 minutes to 48 hours, preferably from 15 minutes to 18 hours, more preferably 15 minutes to 5 hours or from 1 to 5 hours. Said free acid formation can be carried out at normal, elevated or reduced pressure, preferably at normal pressure.

Process Step c2):

In process step c2) the compound of formula I ("the free acid") is formed directly by acidic saponification.

The acid used in step c2) is typically an inorganic acid, such as hydrochloric acid or sulfuric acid; or an organic acid, such as formic acid, acetic acid or propionic acid. Preference is given to inorganic acids and special preference is given to hydrochloric acid.

A preferable amount of acid is at least 0.01 equivalents relative to compounds of formula III, more preferably from 0.01 to 5 equivalents; even more preferably from 1 to 5 equivalents, most preferably from 1 to 3 equivalents.

The formation of the free acid is preferably carried out in a temperature range of from 40° C. to 100° C., especially from 40° C. to 60° C. The reaction time is generally from 15 minutes to 48 hours, preferably from 15 minutes to 18 hours, more preferably 15 minutes to 5 hours or 1 to 5 hours. Said free acid formation can be carried out at normal, elevated or reduced pressure, preferably at normal pressure.

Isolation of Compound of Formula I after Performing Process Step c1) or c2):

Under typical process conditions described above, the compounds of formula I precipitate and can be easily isolated after performing process steps c1) or c2). Typically this is done by cooling followed by filtration.

Methylhydrazine can be used in aqueous diluted form, which is less hazardous then using methylhydrazine in substantially pure form.

FIGURES

Figure 1B:
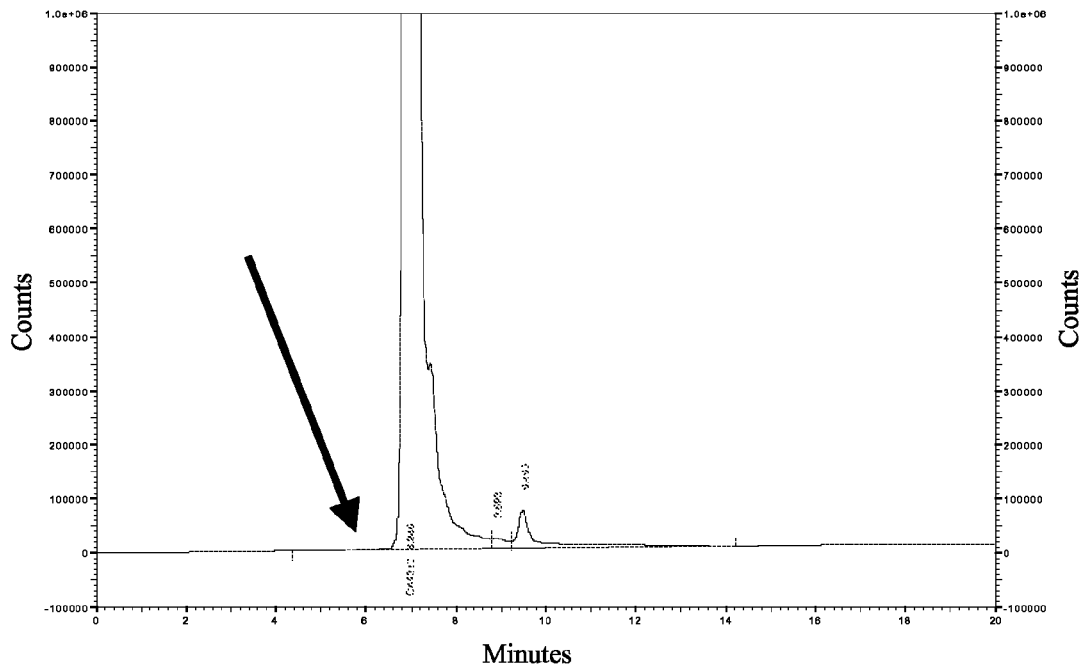

FIGS. 1a and 1b show chromatograms of 3-difluoromethyl-1-methyl-1H-pyrazole-4-carboxylic acid produced according to Examples P1 and P2. FIG. 1a shows a chromatogram of 3-difluoromethyl-1-methyl-1H-pyrazole-4-carboxylic acid in which the ethyl 3-difluoromethyl-1-methyl-1H-pyrazole-4-carboxylate is not treated with base. FIG. 1b shows a chromatogram of 3-difluoromethyl-1-methyl-1H-pyrazole-4-carboxylic acid in which the ethyl 3-difluoromethyl-1-methyl-1H-pyrazole-4-carboxylate is treated with base according to experiment 2 in Table 1. The arrows show the location of the peak corresponding to the impurity. It can be seen that the peak corresponding to the impurity is absent in the chromatogram shown in FIG. 1b. The large peak adjacent to the impurity corresponds to 3-difluoromethyl-1-methyl-1H-pyrazole-4-carboxylic acid.

EXAMPLES

Example P1

Preparation of ethyl 3-difluoromethyl-1-methyl-1H-pyrazole-4-carboxylate

A 0.25 mol solution of methylhydrazine 40% diluted in 50.0 g xylene and 4.7 g water was prepared. A solution of 0.25 mol of 2-[1-Ethoxy-meth-(Z)-ylidene]-4,4-difluoro-3-oxo-butyric acid ethyl ester in 100.0 g xylene was added to the methylhydrazine over 30-60 minutes at a temperature of 20-25° C. The reaction mixture was stirred for 15 min. The phases of the reaction mass were separated.

Example P2

Preparation of 3-difluoromethyl-1-methyl-1H-pyrazole-4-carboxylic acid

To the organic phase obtained in P1 19 g water and 0.51 mol NaOH 30% were added and heated to 60-65° C. The reaction mass was stirred during 45 minutes at 60-65° C. The phases of the reaction mixture were separated at 60-65° C. The alkaline water phase (product phase) was added to a solution of 20.0 g water and 0.54 mol of HCl 32% at 80-85° C. The reaction mass was stirred over 5-10 minutes at 80-85° C. The suspension was cooled down from 80-85° C. to 0-5° C. The suspension was filtered off and crystals washed 2× with 42.5 g of water (0° C., displacement-washing). The product was dried at 60° C. under reduced pressure.

Example 3

Effect of Washing ethyl 3-difluoromethyl-1-methyl-1H-pyrazole-4-carboxylate with Base Gel permeation chromatography was used to detect the presence of oligomeric impurities in the product of Example P2. A peak at retention time 5.93° is attributed to an impurity which correlates strongly with product colour, and with tarring and performance issues in the subsequent chemistry. Reduction of this peak was achieved by washing the product of Example P1 (ethyl 3-difluoromethyl-1-methyl-1H-pyrazole-4-carboxylate) as shown in Table 1, prior to preparation of 3-difluoromethyl-1-methyl-1H-pyrazole-4-carboxylic acid according to Example P2.

TABLE 1

| Experiment | Base | Initial base strength | Base quantity (mole eq) | RT 5.93' (% w/w) |
|---|---|---|---|---|
| 1 | Control-no washing | | | 0.38 |
| 2 | NaOH | 10% | 0.5 | Not detected |
| 3 | NaOH | 10% | 0.2 | 0.01 |
| 4 | NaOH | 2% | 0.1 | 0.11 |
| 5 | NaOH | 10% | 0.1 | 0.15 |
| 6 | $Na_2CO_3$ | 10% | 0.5 | 0.14 |

"Initial base strength" refers to the strength of the base in the aqueous solution prior to addition to the ethyl 3-difluoromethyl-1-methyl-1H-pyrazole-4-carboxylate.

"Base quantity (mole eq) indicates the molar amount of base relative to the molar amount of ethyl 3-difluoromethyl-1-methyl-1H-pyrazole-4-carboxylate.

The peak of interest at retention time 5.93' is reported as % w/w, calibrated using the response factor of the adjacent main peak, i.e., the compound of formula I.

In Table 1, all of the washings described were carried out on a crude solution of ethyl 3-difluoromethyl-1-methyl-1H-pyrazole-4-carboxylate in xylenes at a concentration of approximately 20-25%. The treatment was carried out with the base as described, at ambient temperature, for a period of 40-120 minutes. The analysis is carried out on the subsequently produced product of formula I according to Example P2.

The chromatograms of the control (experiment 1 in table 1) and treated material (experiment 2 in table 1) are shown in FIGS. 1a and 1b.

The treatment of ethyl 3-difluoromethyl-1-methyl-1H-pyrazole-4-carboxylate with base also gave rise to a visual improvement in the colour of the subsequently-produced product of formula I. Table 2 shows a qualitative assessment of the colour of products of formula I produced from base-treated ethyl 3-difluoromethyl-1-methyl-1H-pyrazole-4-carboxylate.

TABLE 2

| Experiment | Base | Initial base strength | Base quantity (mole eq) | Visual description | |
|---|---|---|---|---|---|
| 2 | NaOH | 10% | 0.5 | Almost white | |
| 3 | NaOH | 10% | 0.2 | Cream | |
| 4 | NaOH | 2% | 0.1 | Pale fawn | Increasing darkness |
| 5 | NaOH | 10% | 0.1 | Fawn | |
| 6 | $Na_2CO_3$ | 10% | 0.5 | Fawn | |
| 1 | Control—no washing | | | brown | |

The increase in purity may also be confirmed using HPLC.

Comparative Example

Xylene Washing of the Sodium Salt of 3-difluoromethyl-1-methyl-1H-pyrazole-4-carboxylic acid A small portion of crude aqueous solution of the sodium salt of the product of Example P2 was briefly washed with an equal portion of xylenes. The phases were then separated. The xylene phase remained almost colourless while the aqueous phase was unchanged in colour, indicating no oligomer removal.

The invention claimed is:

1. A process for washing a compound of formula III with aqueous alkali

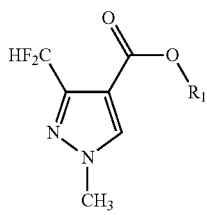

wherein $R^1$ is $C_1$-$C_6$ alkyl and $R^2$ is $CF_3$, $CF_2H$ or $CFH_2$, comprising the steps of
　a) contacting a compound of formula III with an aqueous base by adding the base to the compound of formula III as an aqueous solution, or adding base and water separately to the compound of formula III, and
　b) separating the compound of formula III and the base by removing the aqueous phase.

2. The process of claim 1, wherein the amount of base used in step a) is 1 molar equivalent or less relative to the amount of the compound of formula III.

3. The process of claim 1, wherein the amount of base used in step a) is 0.1 to 0.5 molar equivalents relative to the amount of the compound of formula III.

4. The process of claim 1, wherein the base is a salt of an alkali metal or an alkali earth metal.

5. The process of claim 4, wherein the base is a hydroxide or a carbonate salt.

6. A method of purifying a compound of formula III:

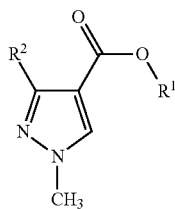

wherein $R^1$ is $C_1$-$C_6$ alkyl and $R^2$ is $CF_3$, $CF_2H$ or $CFH_2$, for use as a reactant in a process for the production of a compound of formula I

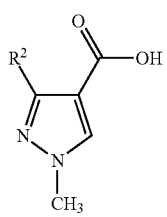

wherein $R^2$ is $CF_3$, $CF_2H$ or $CFH_2$, comprising washing a compound of formula III as defined in claim 1.

7. A process comprising
i. producing a compound of formula III

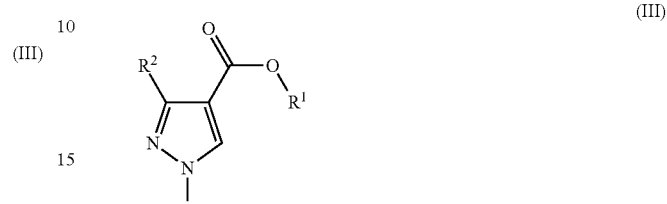

wherein $R^1$ is $C_1$-$C_6$ alkyl and $R^2$ is $CF_3$, $CF_2H$ or $CFH_2$, comprising reacting a compound of formula II

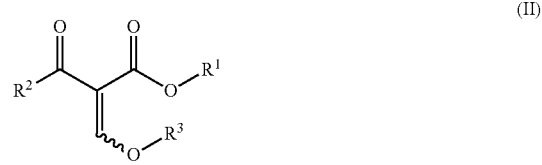

wherein $R^1$ and $R^3$ are both independently $C_1$-$C_6$alkyl and $R^2$ is $CF_3$, $CF_2H$ or $CFH_2$, with methylhydrazine to form a compound of formula III; and ii. washing the compound of formula III as defined in claim 1, and iii hydrolyzing the compound of formula III to produce the compound of formula I.

8. A method of producing a compound of formula IV

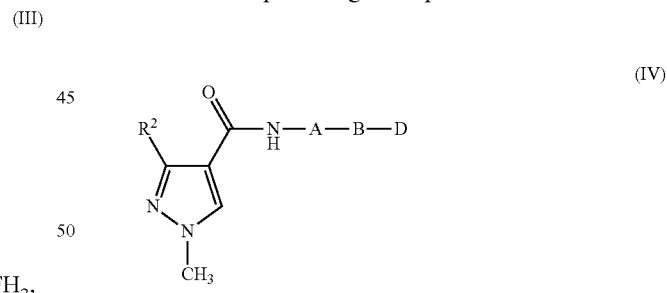

wherein $R^2$ is $CF_3$, $CF_2H$ or $CFH_2$,

A is thienyl, phenyl, or ethylene each optionally substituted by one to three groups independently selected from halogen, methyl and methoxy, B is a direct bond, cyclopropylene, an annelated bicyclo[2.2.1]heptane- or bicyclo[2.2.1]heptene ring, D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio, comprising producing a compound of formula I

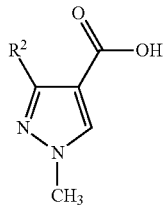
(I)

wherein R² is CF₃, CF₂H or CFH₂, as defined in claim 7, and iv) reacting the compound of formula I or the corresponding acid-halide with a compound of formula V

H₂N-A-B-D            (V)

wherein A, B and D are as defined for the compound of formula IV.

9. A process according to claim 8, wherein the compound of formula IV is a compound of formula VI (Isopyrazam), a compound of formula VII (Sedaxane), a compound of formula VIII, a compound of formula IX (Penthiopyrad), a compound of formula X (Bixafen), a compound of formula XI (Fluxapyroxad), a compound of formula XII, or a compound of formula XIII

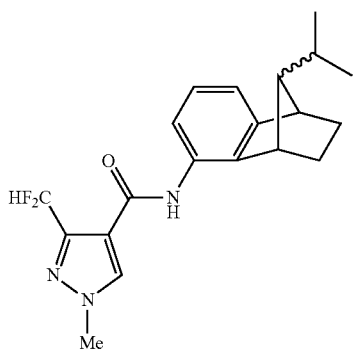
(VI)

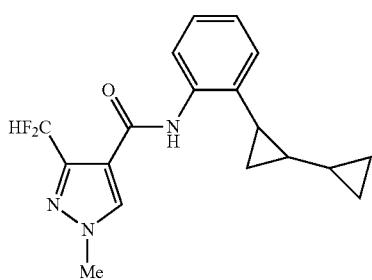
(VII)

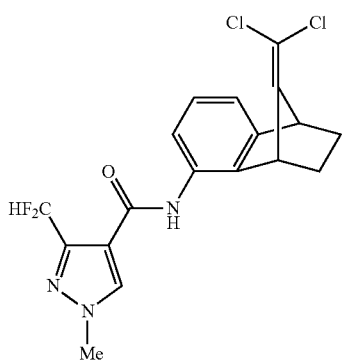
(VIII)

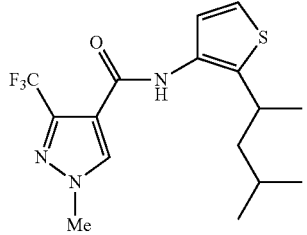
(IX)

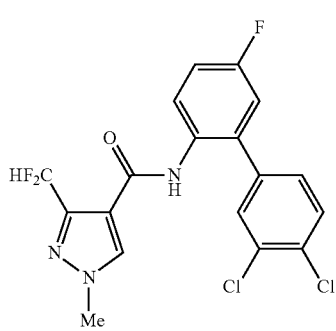
(X)

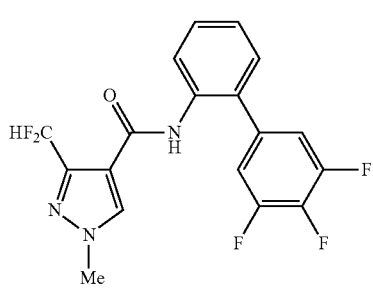
(XI)

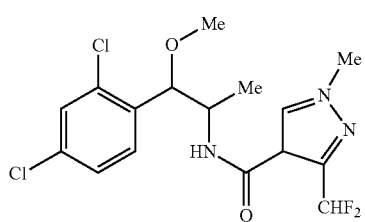
(XII)

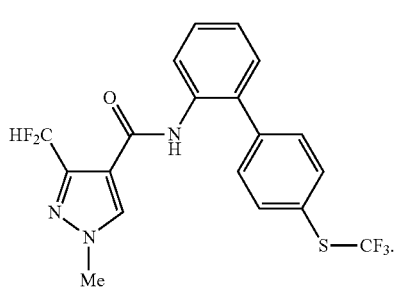
(XIII)

10. The process of claim 1, wherein R¹ is ethyl.
11. The process of claim 1, wherein R² is CF₂H.

12. A process comprising i. producing a compound of formula III

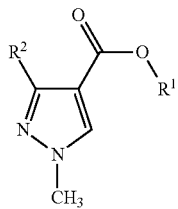
(III)

wherein $R^1$ is $C_1$-$C_6$ alkyl and $R^2$ is $CF_3$, $CF_2H$ or $CFH_2$, comprising reacting a compound of formula II

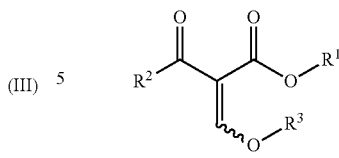
(II)

wherein $R^1$ and $R^3$ are both independently $C_1$-$C_6$alkyl and $R^2$ is $CF_3$, $CF_2H$ or $CFH_2$, with methylhydrazine without the addition of a base to form a compound of formula III; and ii. washing the compound of formula III as defined in claim 1.

13. The use of an aqueous alkali to remove oligomeric impurities from a composition comprising a compound of formula III as defined in claim 1.

\* \* \* \* \*